United States Patent
Matz et al.

(10) Patent No.: US 11,448,551 B2
(45) Date of Patent: Sep. 20, 2022

(54) OPTICAL ARRANGEMENT FOR A SPECTROSCOPIC IMAGING METHOD AND SPECTROSCOPIC IMAGING METHOD

(71) Applicant: GRINTECH GmbH, Jena (DE)

(72) Inventors: Gregor Matz, Göttingen (DE); Bernhard Messerschmidt, Jena (DE)

(73) Assignee: GRINTECH GmbH, Jena (DE)

( * ) Notice: Subject to any disclaimer, the term of this patent is extended or adjusted under 35 U.S.C. 154(b) by 0 days.

(21) Appl. No.: 17/055,069

(22) PCT Filed: May 20, 2019

(86) PCT No.: PCT/EP2019/062954
§ 371 (c)(1),
(2) Date: Nov. 12, 2020

(87) PCT Pub. No.: WO2019/224146
PCT Pub. Date: Nov. 28, 2019

(65) Prior Publication Data
US 2021/0215535 A1   Jul. 15, 2021

(30) Foreign Application Priority Data

May 22, 2018   (DE) .......................... 102018112253.5

(51) Int. Cl.
*G01J 3/02* (2006.01)
*A61B 5/00* (2006.01)
(Continued)

(52) U.S. Cl.
CPC ........ *G01J 3/0208* (2013.01); *A61B 1/00096* (2013.01); *A61B 1/00167* (2013.01);
(Continued)

(58) Field of Classification Search
CPC .......... G01J 3/0208; G01J 3/0218; G01J 3/44; G01J 3/021; A61B 5/0075; A61B 5/0084;
(Continued)

(56) References Cited

U.S. PATENT DOCUMENTS 6,697,192 B1   2/2004 Fan et al.
7,414,729 B2   8/2008 Xie et al.
(Continued)

FOREIGN PATENT DOCUMENTS

DE   102009011647 A1   9/2010
DE   102016003334 A1   9/2017

OTHER PUBLICATIONS

A. Lombardini, "High-resolution multimodal flexible coherent Raman endoscope," Cornell University Library, Aug. 11, 2017, 29 pages.
(Continued)

*Primary Examiner* — Dominic J Bologna
(74) *Attorney, Agent, or Firm* — Slater Matsil, LLP

(57) ABSTRACT

In an embodiment an optical arrangement includes a multicore fiber having at least a first fiber core configured to guide a first illumination light and a second fiber core configured to guide a second illumination light, wherein the multicore fiber comprises a fiber scanner configured to deflect the multicore fiber or the multicore fiber is followed by a mirror scanner; and a wavelength dispersive beam combiner configured to spatially superimpose the first illumination light and the second illumination light in an object space.

15 Claims, 4 Drawing Sheets

(51) Int. Cl.
*G01J 3/44* (2006.01)
*G01N 21/65* (2006.01)
*G02B 6/02* (2006.01)
*G02B 6/024* (2006.01)
*G02B 26/10* (2006.01)
*G02B 27/12* (2006.01)
*A61B 1/00* (2006.01)
*G02B 27/10* (2006.01)
*A61B 1/06* (2006.01)
*A61B 1/07* (2006.01)

(52) U.S. Cl.
CPC ........ *A61B 1/00172* (2013.01); *A61B 1/0638* (2013.01); *A61B 1/07* (2013.01); *A61B 5/0075* (2013.01); *A61B 5/0084* (2013.01); *G01J 3/021* (2013.01); *G01J 3/0218* (2013.01); *G01J 3/44* (2013.01); *G01N 21/65* (2013.01); *G02B 6/024* (2013.01); *G02B 6/02042* (2013.01); *G02B 26/103* (2013.01); *G02B 27/1093* (2013.01); *G02B 27/126* (2013.01); *G01N 2021/653* (2013.01); *G01N 2021/655* (2013.01); *G01N 2201/0853* (2013.01); *G01N 2201/0866* (2013.01)

(58) Field of Classification Search
CPC ............ A61B 1/00096; A61B 1/00167; A61B 1/00172; A61B 1/0638; A61B 1/07; G01N 21/65; G01N 2021/653; G01N 2021/655; G01N 2201/0853; G02B 6/02042; G02B 6/024; G02B 26/103; G02B 27/126; G02B 27/1093
See application file for complete search history.

(56) References Cited

U.S. PATENT DOCUMENTS

| | | |
|---|---|---|
| 8,526,110 B1 | 9/2013 | Honea et al. |
| 8,582,096 B2 | 11/2013 | Chen et al. |
| 9,145,346 B1 | 9/2015 | Hoyme et al. |
| 9,146,346 B2 | 9/2015 | Paré et al. |
| 2005/0038322 A1* | 2/2005 | Banik ................ A61B 1/00103 600/129 |
| 2007/0088219 A1* | 4/2007 | Xie ...................... A61B 5/0066 600/473 |
| 2007/0104431 A1 | 5/2007 | Di Teodoro et al. |
| 2011/0282166 A1 | 11/2011 | Chen et al. |
| 2014/0212083 A1* | 7/2014 | Pare .................... H01S 3/06733 385/11 |
| 2016/0022119 A1* | 1/2016 | Shahmoon ............ G02B 23/26 600/182 |
| 2016/0357007 A1 | 12/2016 | Swanson |
| 2018/0120555 A1* | 5/2018 | Ikuta ................... A61B 1/0638 |

OTHER PUBLICATIONS

X. Chen, et al., "Multmodal Nonlinear Endo-Microscopy Probe Design for High Resolution, Label-Free Intraoperative Imaging," Optical Society of America, Jul. 1, 2015, 11 pages, vol. 6, No. 7.
P. Deladurantaye et al., "Advances in Engineering of High Contrast CARS Imaging Endoscopes," Optical Society of America, Oct. 20, 2014, 12 pages, vol. 22, No. 21.
C. Lee, et al., "Scanning Fiber Endoscopy With Highly Flexible, 1 mm Catheterscopes for Wide-Field, Full-Color Imaging," Journal of Biophotonics 3, No. 2010, No. 5-6, pp. 385-407.
Z. Wang, et al., "Coherent Anti-Stokes Raman Scattering Microscopy Imaging With Suppression of Four-Wave Mixing in Optical Fibers," Optical Society of America, Apr. 25, 2011, 11 pages, vol. 19, No. 9.

* cited by examiner

OPTICAL ARRANGEMENT FOR A SPECTROSCOPIC IMAGING METHOD AND SPECTROSCOPIC IMAGING METHOD

This patent application is a national phase filing under section 371 of PCT/EP2019/062954, filed May 20, 2019, which claims the priority of German patent application 102018112253.5, filed May 22, 2018, each of which is incorporated herein by reference in its entirety.

TECHNICAL FIELD

The application concerns an optical arrangement for a spectroscopic imaging method. The application also concerns a spectroscopic imaging method using the optical arrangement.

The optical arrangement may in particular be intended for an endoscopic probe designed for spectroscopic imaging of voluminous samples, e.g. living biological tissue. In particular, as imaging method a nonlinear spectroscopic process can be used, especially Coherent Anti-Stokes Raman Scattering (CARS) or Stimulated Raman Scattering (SRS). To enable this modality, two light pulses of high peak intensity and different frequency may be superimposed simultaneously at the same location in the sample.

BACKGROUND

U.S. Pat. No. 7,414,729 B2 describes an endoscopic probe for CARS spectroscopy, where the illumination light with two different wavelengths, the Pump and Stokes wavelength, is guided to the sample through the same optical fiber.

When guiding the Pump and Stokes wavelengths in a single fiber, the problem can arise that the simultaneous superposition of the highly intense light pulses leads to a nonlinear four-wave mixing process, in which light is generated that has the same optical frequency as the sample signal to be measured. If this high-intensity, non-resonant background reaches the sample to be analyzed, it is no longer possible to distinguish it from the low-intensity signal of the sample to be measured. Therefore it is important to place a short pass filter or band pass filter in the beam path, which is optically opaque to the non-resonant background and only conducts the pump and Stokes wavelength to the sample. However, this is accompanied by the fact that also the CARS signal from the sample cannot be collected by the same beam path from the sample to the fiber, which requires a second beam path to collect the sample signal with the Anti-Stokes wavelength and thus limits the miniaturization of the system.

SUMMARY

Embodiments provide an optical arrangement for a spectroscopic imaging method which avoids the problem of the occurrence of a non-linear four-wave mixing process and at the same time exhibits a compact design. Further embodiments provide a spectroscopic imaging method which makes use of the optical arrangement.

According to at least one embodiment, the optical arrangement for a spectroscopic imaging method comprises a multi-core fiber comprising at least a first fiber core for guiding a first illumination light and a second fiber core for guiding a second illumination light. The fiber is designed in particular as a double-core fiber and can thus advantageously guide the first illumination light and the second illumination light simultaneously, the first illumination light and the second illumination light comprising in particular different wavelengths. The fiber cores preferably comprise different diameters and/or different materials. In this way, the single mode and at the same time a good light guidance for the respective wavelength can be ensured.

For scanning the object space, the multicore fiber comprises a fiber scanner for deflection of the multicore fiber according to a design of the optical arrangement. The fiber scanner can be designed as a piezo scanner, for example. According to an alternative design, the multi-core fiber is followed by a mirror scanner. The mirror scanner can in particular be designed as a MEMS scanner. By the fiber scanner or the mirror scanner a time-dependent beam deflection is realized, which enables the imaging.

Furthermore, the optical arrangement includes a wavelength dispersive beam combiner configured to spatially and angularly superimpose the first illumination light and the second illumination light in an object space. The optical arrangement can be part of a microscopic arrangement, in particular the optical arrangement can be integrated into an endoscopic probe which is part of a fiber optic endomicroscope.

The fact that the first illumination light and the second illumination light in the optical arrangement are guided through different fiber cores of the multi-core fiber advantageously prevents a nonlinear four-wave mixing process that can occur when both wavelengths are guided in the same fiber. At the same time, no further beam path is required in a second fiber, so that the optical arrangement can exhibit a particularly compact design.

The spectroscopic imaging method for which the optical arrangement is intended can be CARS spectroscopy or SRS spectroscopy in particular. In the method, two light pulses of the first illumination light and the second illumination light with different wavelengths are superimposed simultaneously at the same location of a sample in the object space.

In particular, in the first fiber core, the first illumination light of the pump wavelength is guided and in the second fiber core, the second illumination light of the Stokes wavelength is guided. By separately guiding the pump wavelength and the Stokes wavelength in the two fiber cores, the undesired four-wave mixing process is sufficiently suppressed. The first illumination light and the second illumination light are generated in particular by a laser light source and are coupled into an end of the multicore fiber that faces away from the object space. The frequency difference of the two wavelengths is advantageously tuned to a molecular intrinsic vibration of the sample to be detected in such a way that it drives the sample coherently and leads to the emission of a third wavelength, the anti-Stokes wavelength, which is used for spectroscopic imaging. Furthermore, the presented principle allows the simultaneous imaging of additional nonlinear imaging processes such as higher-harmonic microscopy and multiphoton fluorescence microscopy.

According to an advantageous embodiment, the wavelength-selective beam combiner is located between the fiber scanner or the mirror scanner and the object space. In this case, the first illumination light and the second illumination light are deflected to scan the object space before they are combined by the wavelength-selective beam combiner, for example a grating or a prism. The first illumination light and the second illumination light are deflected in the same way by the fiber scanner or the mirror scanner in particular, whereby the following wavelength-selective beam combiner is advantageously unmoved.

According to an embodiment a collimating lens is arranged between the fiber scanner or the mirror scanner and the wavelength-selective beam combiner. The collimating lens can be a one-piece or multi-piece lens. In a preferred configuration, the collimating lens includes a gradient index lens (GRIN lens). For the beam combination of the first and second illumination light by means of the wavelength-selective beam combination element, it is advantageous if an at least approximate collimation of the illumination lights of both wavelengths takes place before the wavelength-selective beam combination element. A local offset of the first and second illumination light when exiting the multicore fiber can be used to create an angular offset, for example, by means of the collimating lens. The wavelength-selective beam combiner element is advantageously located in the Fourier plane of the imaging optics behind the fiber scanner or mirror scanner, i.e. in particular behind the collimating lens.

The optical arrangement described here allows a very good diffraction limited imaging quality for CARS imaging over a comparatively large image field with respect to the total diameter of the optical arrangement. In particular, higher order aberrations, which could restrict the usable field of view, are largely avoided by the optical arrangement.

According to an advantageous configuration of the optical arrangement, the multi-core fiber contains a light-guiding cladding for guiding object light coming from the object space. The light-guiding cladding is surrounded by an outer cladding which comprises a lower refractive index than the light-guiding cladding. In the multi-core fiber, in particular not only the illumination light is guided in the direction of the object space, but advantageously also the object light to be detected is guided in the opposite direction to an evaluation unit.

According to an advantageous configuration, the multi-core fiber comprises an inner cladding in which the fiber cores are arranged, the inner cladding being surrounded by the light-guiding cladding. The inner cladding advantageously comprises a lower refractive index than the fiber cores and a lower refractive index than the light guiding cladding. In particular, the inner cladding allows a single-mode light-guiding property of the two fiber cores to be achieved. The inner cladding can be doped with fluorine in particular. The light-guiding cladding, which is located between the inner cladding and the outer cladding and comprises a higher refractive index, can be used efficiently for collecting the object light.

The fiber cores of the multicore fiber are preferably made of quartz glass. The inner cladding and the outer cladding of the multicore fiber can be doped with a dopant such as fluorine to lower the refractive index. The light conducting cladding preferably comprises pure quartz glass or is doped with a suitable dopant such as germanium oxide to increase the refractive index.

According to an advantageous configuration, the multi-core fiber is a polarization-maintaining fiber. In order to achieve the polarization-maintaining property, the multi-core fiber may contain stress generating elements which cause a birefringent property by generating a permanent stress. The stress-generating elements can be rod-shaped, for example.

According to a further configuration of the multicore fiber, the fiber cores are asymmetrically arranged in the multicore fiber.

In particular, the fiber cores are arranged asymmetrically to the center of the multicore fiber. For example, the fiber cores may comprise different distances from the center of the multicore fiber. Furthermore, the fiber cores can be arranged one after the other in the same radial direction as seen from the center of the multicore fiber. Depending on how much the object light to be detected differs in wavelength from the wavelengths of the illumination light guided in the fiber cores, the object light is also deflected by the wavelength dispersive beam combiner so that it does not strike the fiber end face centrally. This can impair the collecting efficiency of the fiber for the object light. For this reason, it can be advantageous to arrange the fiber cores asymmetrically in the multicore fiber, especially off-center to the light-guiding cladding.

The wavelength dispersive beam combiner of the optical arrangement may comprise different configurations. In particular, the beam combiner can be a diffraction grating, for example a reflection diffraction grating or a transmission diffraction grating. In a configuration, the beam combiner is a reflection diffraction grating so that the optical axis is angled towards the object space. Alternatively, the beam combiner can comprise at least one prism or grating prism (GRISM), where the grating prism is a combination of a diffraction grating and a prism. In another configuration, the beam combiner is a multiple prism, where the optical axis preferably does not change its direction. It is also possible that the beam combiner is a prism or a multiple prism and the direction of the optical axis changes in a targeted manner towards the object space. The wavelength-dispersive beam combiner can be located, for example, between the fiber scanner or mirror scanner and the object space. Alternatively, the wavelength dispersive beam combiner can be placed between the multi-core fiber and the mirror scanner.

The optical arrangement can contain further elements in addition to the components described above. In a configuration, the optical arrangement contains for example the fiber scanner, a gradient index lens (GRIN lens), the wavelength-sensitive deflection element as well as a front lens group facing the object space, which comprises for example a spherical achromatic lens, a biconvex lens and a plano-convex lens. In another configuration, the optical arrangement contains a mirror scanner, a GRIN lens, a deflection prism, a spherical meniscus lens, a spherical achromatic lens, the wavelength-sensitive deflecting element and a front lens group facing the object space, comprising for example a spherical achromatic lens, a biconvex lens and a plano-convex lens.

The numerical aperture of the multicore fiber is preferably between 0.05 and 0.4, and the numerical aperture of the optical arrangement to the object space is preferably between 0.2 and 1.1.

According to an advantageous configuration, the optical arrangement comprises a diameter of less than 5 mm. The small diameter is made possible in particular by the fact that the optical arrangement comprises only one beam path between the multi-core fiber and the object space for the illumination light and the object light to be detected.

Yet further embodiments provide an endoscopic probe which contains the optical arrangement. The endoscopic probe can be a component of a fiber-optic endomicroscope which comprises in particular the fiber-optic probe, an illumination light source for generating the first and second illumination light and an evaluation unit.

In the spectroscopic imaging method according to the principle proposed herein, a first illumination light is guided in a first fiber core of a multi-core fiber and a second illumination light is guided in a second fiber core of the multi-core fiber, the first illumination light and the second illumination light comprising different wavelengths. The first illumination light and the second illumination light are spatially superimposed in an object space by a wavelength dispersive beam combiner. The object light coming from the object space is guided in a light-guiding cladding of the multicore fiber towards an evaluation unit.

In this method the multi-core fiber is advantageously integrated into a fiber scanner, which deflects the fiber perpendicular to the exit direction of the light, or a mirror scanner follows the multi-core fiber, whereby the object space is scanned by the movement of the fiber scanner or the mirror scanner. In this case, only one optical beam path is formed between the multi-core fiber and the object space, in which the first and second illumination light is guided in the direction of the object space, and in which the object light is guided in the opposite direction to the multi-core fiber. The spectroscopic imaging method can in particular be CARS spectroscopy or SRS spectroscopy, wherein the first illumination light comprises the pump wavelength and the second illumination light comprises the Stokes wavelength.

Further advantageous configurations of the method result from the description of the optical arrangement and vice versa.

BRIEF DESCRIPTION OF THE DRAWINGS

The invention is described in the following on the basis of exemplary embodiments in connection with FIGS. 1 to 10 in more detail.

In the Figures.

DETAILED DESCRIPTION OF ILLUSTRATIVE EMBODIMENTS

Similar or similarly acting components are marked with the same reference signs in the figures. The shown components as well as the proportions of the components among each other are not to be regarded as true to scale.

Figure 1A:
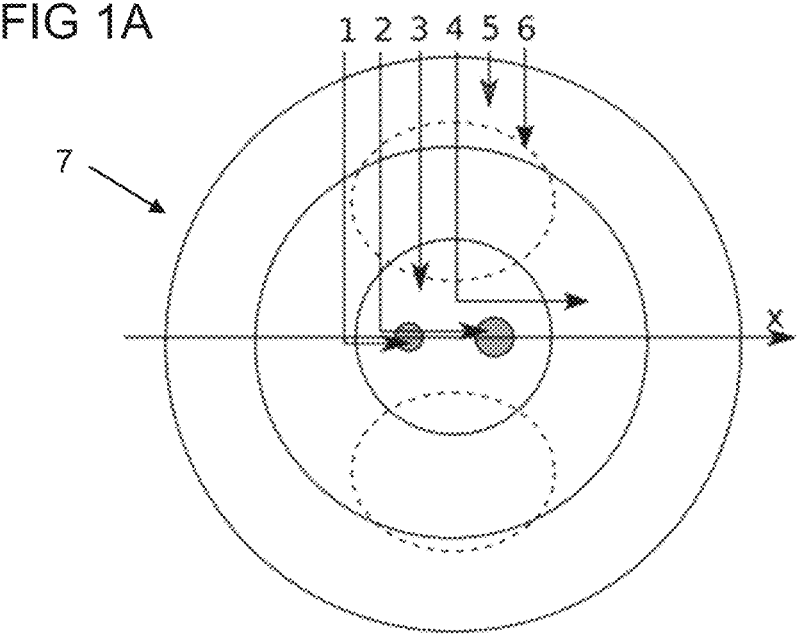
FIG. 1A shows a schematic representation of a cross-section through a first example of multicore fiber.
Figure 1B:
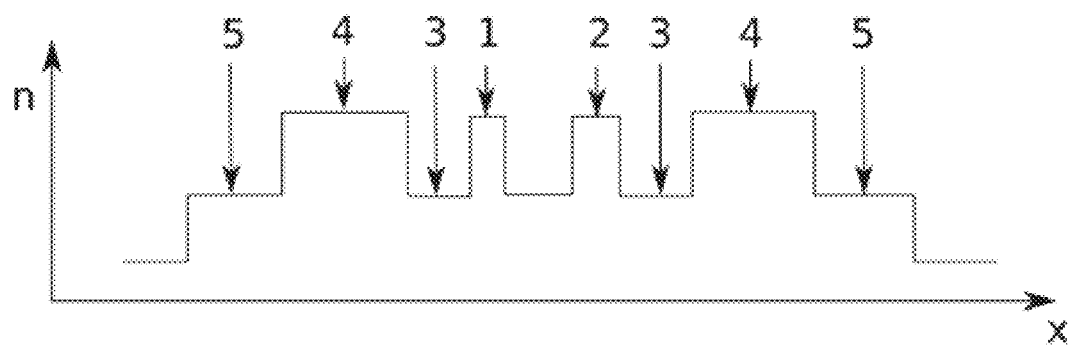
FIG. 1B shows a schematic diagram of the refractive index curve in the multicore fiber according to the first example.

The optical arrangement and the method according to the principle proposed here are based in particular on the use of a multi-core fiber with several claddings, in particular a dual-core double cladding fiber. An example of a multi-core fiber 7 is shown in FIG. 1A. FIG. 1B shows schematically the course of the refractive index n across the cross-section of the multicore fiber in the direction x, which is shown in FIG. 1A.

The multicore fiber 7 has two fiber cores 1, 2. The first fiber core 1 carries a first illumination light, in particular the light of the pump wavelength for CARS spectroscopy or SRS spectroscopy. The second fiber core 2 carries a second illumination light, which comprises a wavelength different from the wavelength of the first illumination light, in particular the light of the Stokes wavelength for CARS spectroscopy or SRS spectroscopy.

Preferably, both fiber cores 1, 2 have different diameters or materials in order to ensure single-mode and at the same time good light guidance for the respective wavelength. If the fiber cores 1, 2 are made of undoped fused silica, this also reduces the undesired multiphoton self-fluorescence in the fiber and thus ensures better contrast, for example for multiphoton fluorescence microscopy.

These two fiber cores 1, 2 are advantageously embedded in a fluorine-doped inner cladding 3, which comprises a lower refractive index than the two fiber cores 1, 2. This way, especially a single-mode light transmission property of the two fiber cores 1, 2 can be achieved. Radially outside of the inner cladding 3 follows a medium cladding, which in the optical arrangement acts as a light-guiding cladding 4 for the object light to be detected. The light-guiding cladding 4 comprises a higher refractive index than the inner cladding 3 and is therefore light-guiding. The light-guiding cladding 4 can be efficiently used for the integral collection of the object light, for example the CARS, SHG or fluorescence signal of a sample, which is generated in a nonlinear imaging process.

The light-guiding cladding 4 is surrounded by an outer cladding 5, which comprises a lower refractive index than the light-guiding cladding 4, thus enabling the light guiding of the generated object light in the light-guiding cladding 4.

The multicore fiber 7 is preferably a polarization-maintaining fiber. A polarization-maintaining fiber is advantageous for a nonlinear imaging process because the use of polarized light minimizes the required peak intensity and thus reduces damage to the object under examination. The polarization-maintaining property of the multi-core fiber 7 can be achieved in particular by the insertion of stress-generating elements 6, which cause an asymmetrical light guiding property of the fiber cores 1, 2.

Figure 1C:
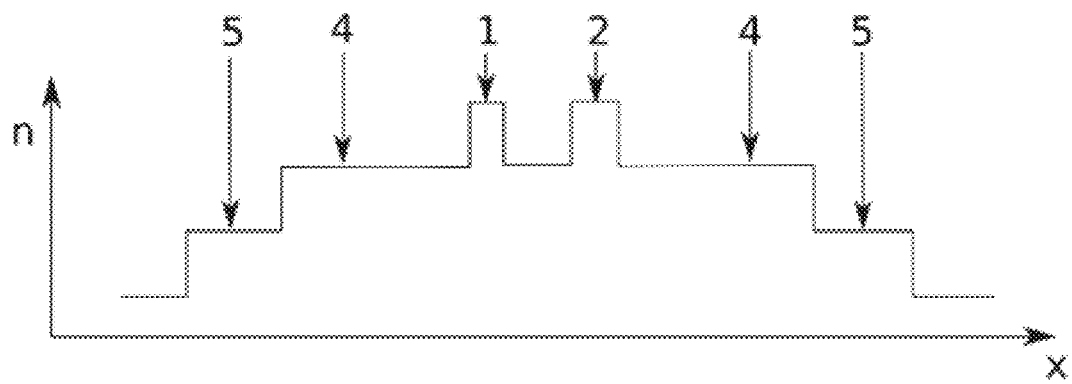
FIG. 1C shows a schematic diagram of the refractive index curve in another example of the multicore fiber.

FIG. 1C shows the refractive index curve in an alternative configuration of the multicore fiber. The light conduction in the fiber cores 1, 2 is realized by the higher refractive index with respect to the light-guiding cladding 4, which is realized for example with a dopant such as germanium.

Figure 1D:
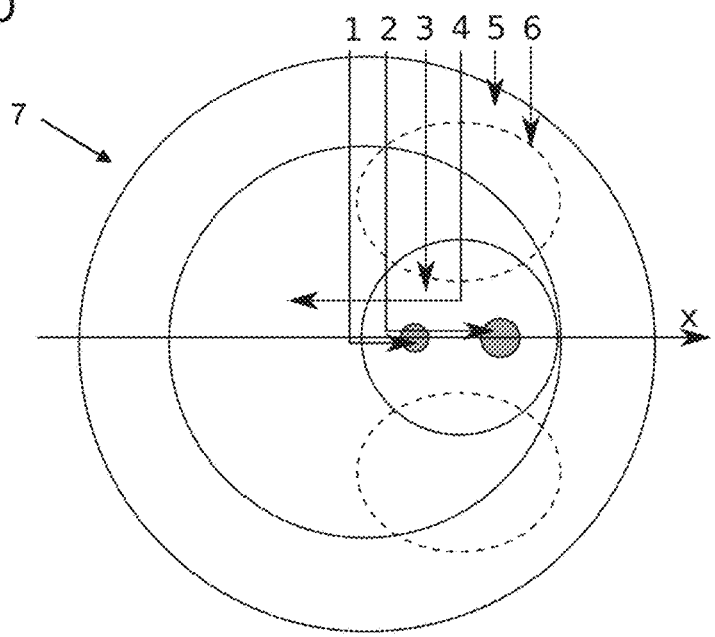
FIG. 1D shows a schematic representation of a cross-section through another example of the multi-core fiber.

FIG. 1D illustrates another possible configuration of the multi-core fiber 7. In this example, the two fiber cores 1, 2 are asymmetrically arranged in the multi-core fiber 7, especially off-center with respect to the light-guiding cladding 4. This arrangement of the fiber cores 1, 2 is especially advantageous if the object light to be detected is deflected by the wavelength-dispersive beam combiner 12 in such a way that it does not strike the fiber end face centrally.

Figure 2:
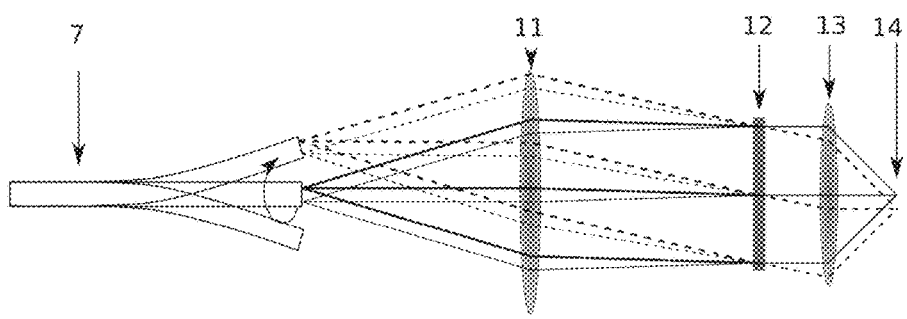
FIGS. 2 to 10 show each a schematic representation of a cross-section through an example of the optical arrangement.

A first example of the optical arrangement for a spectroscopic imaging method is shown in FIG. 2. In the spectroscopic imaging method, for example, the light of an external laser unit serving as an illumination light source is spectrally divided and separately coupled into the fiber cores 1, 2 of the multicore fiber 7 as first illumination light and second illumination light. The multicore fiber 7 emits the light of the two wavelengths with a certain NA and a spatial offset, which corresponds to the distance between the first fiber core 1 and the second fiber core 2.

A subsequent collimating lens 11 leads to an approximate collimation of the illumination light of both wavelengths. The local offset at the fiber exit becomes a wavelength-specific angular offset, which is then spatially and angularly superimposed by a laterally wavelength-dispersive beam combiner 12. A subsequent front lens group 13 now focuses the beams of illumination light with a sufficiently high NA in object space 14 to meet the phase matching conditions and peak intensities required for imaging processes. The object light to be detected in object space can be an Antistokes signal, a SHG signal (Second Harmonic Generation) and/or a TPF signal (Two-Photon Fluorescence). The object light is returned to the same beam path in the optical arrangement and integrally collected by the light guiding cladding of the multi-core fiber 7.

The distal end of the multi-core fiber 7 is equipped with a fiber scanner (not shown) to deflect the multi-core fiber in the example in FIG. 2. By laterally deflecting the fiber end face, e.g. using a piezo fiber scanner or another suitable method, the object space 14 is scanned according to the magnification of the optical arrangement. Due to the concordant movement of the light-guiding cladding of the multi-core fiber 7, it acts as a quasi-confocal optical detector for the signal emitted by the sample in the volume around the excitation spot. Depending on the size and numerical aperture of the light-guiding cladding 4 of the multicore fiber 7, the confocality can be influenced. For high collection efficiency, the medium light-guiding cladding 4 of the multi-core fiber 7 should be as large as possible so that the volume around the excitation spot in which the object light to be detected is scattered is also covered by the light-guiding cladding.

Depending on how much the object light of the sample to be detected differs in wavelength from the wavelengths of the illumination light guided in the fiber cores 1, 2, the object light is also deflected by the wavelength-dispersive beam combiner 12 so that it does not strike the fiber end face centrally. This may affect the collection efficiency of the multicore fiber 7 for the object light. Therefore, it may be advantageous to arrange the area of the two fiber cores 1 and 2 off-center with respect to the light-guiding cladding 4 or to design it asymmetrically, as in the example of the multicore fiber 7 according to FIG. 1D. On the other hand, this increases the manufacturing effort and, in the case of an enlargement of the cross-section, the stiffness of the multi-core fiber 7, which results in a spatial enlargement and increased energy consumption of the scanner in order to ensure the necessary lateral deflection for scanning the object space 14. A technically reasonable compromise can be found here.

For imaging, for example, a photomultiplier (PMT) or a spectrometer triggered in coordination with the excitation signal can be used at the proximal end of the multi-core fiber 7 as a detector of the light emitted by the sample. It is advantageous that no second beam path is required in the optical arrangement to collect the object light and no cleaning filters have to be used in the optical arrangement, since the undesired four-wave mixing process within the multi-core fiber 7 is sufficiently suppressed by the separate guiding of the illumination light with the Stokes wavelength and the illumination light with the pump wavelength.

Figure 3:
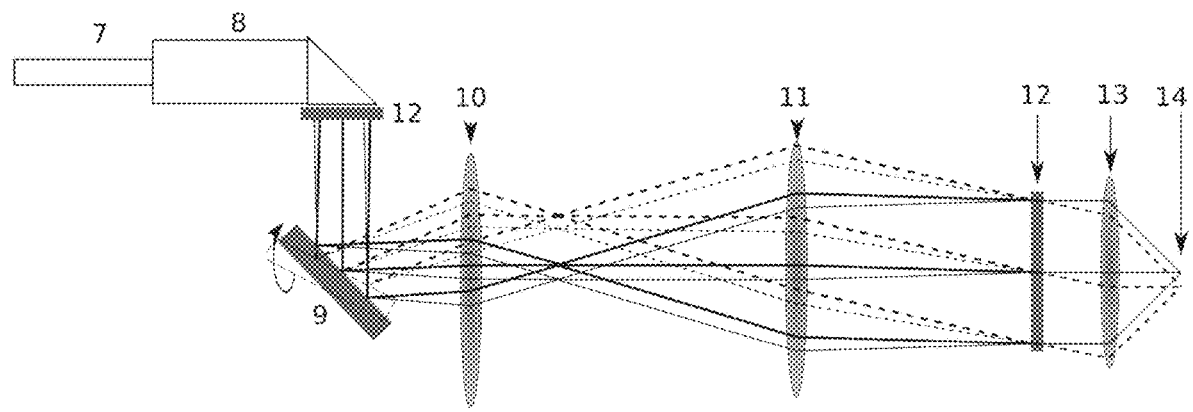

A second example of the optical arrangement is shown in FIG. 3. In this example, the multicore fiber 7 is followed by a collimation unit 8 and a mirror scanner 9. The mirror scanner 9 is a MEMS mirror scanner. A lens 10 following the mirror scanner 9 generates an intermediate image which is then guided into the object space 14 by a lens group acting as a further collimation unit 11, the wavelength dispersive beam combiner 12 and the front lens group 13. Analogous to the example in FIG. 2, the first and second illumination light, especially the light of the pump wavelength and Stokes wavelength, are spatially and angularly combined by the beam combiner 12. The beam combiner 12 can be a linear diffraction grating, for example.

The position of the beam combiner 12 can be chosen differently in this configuration of the optical arrangement, since there are two Fourier planes in this arrangement. Accordingly, the beam combiner 12 can be positioned either directly after the collimation unit 8 or after the further collimation unit 11.

Figure 4:
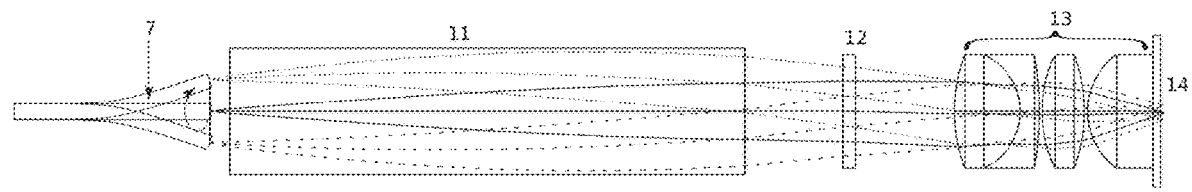

FIG. 4 shows another example of the optical arrangement. In this and every other example, a multicore fiber 7 is used. In the multicore fiber 7, for example, the centers of the two fiber cores 1, 2 in the plane shown are 24 µm apart from one another and comprise a numerical aperture for the Pump and Stokes wavelength of 0.12. The collimation unit 11 is designed as a GRIN lens and collimates in the optical arrangement the illumination light which emerges from the multi-core fiber which is designed as a fiber scanner. Subsequently, the illumination light is spatially and angularly superimposed by the wavelength-dispersive beam combiner element 12, which is, for example, a linear transmission diffraction grating and generates a wavelength-dependent diffraction angle. Here, the grating lines of the transmission diffraction grating are arranged orthogonal to the spatial offset of the fiber cores 1, 2.

A subsequent front lens group 13, which corrects chromatic and other imaging errors via the image field and consists, for example, of an achromatic and two spherical singlet lenses, focuses the light with a numerical aperture of, for example, about 0.54 into the object space 14, where the spectroscopic imaging, nonlinear CARS process on a sample takes place. An NA of at least 0.15 is advantageous, especially to ensure the condition of pulse conservation. The generated signal is subsequently guided back to the multi-core fiber 7 on the same path and collected by the light-guiding cladding 4.

An estimation for the paraxial case can be found according to the following rule for the grating period of the beam combiner element 12 designed as a transmission diffraction grating: $g=(f*\Delta\lambda/\lambda)/a$. The grating period g is given in µm per line, f is the focal length of the collimation unit 11, $\Delta\lambda$ is the wavelength difference between the pump and Stokes wavelengths, and a is the distance between the centers of the two fiber cores 1, 2. In the example shown, f=3.92 mm, $\Delta\lambda$=245 nm and a=24 µm, resulting in a grating period of the beam combiner 12 of 40 µm per line.

Figure 5:
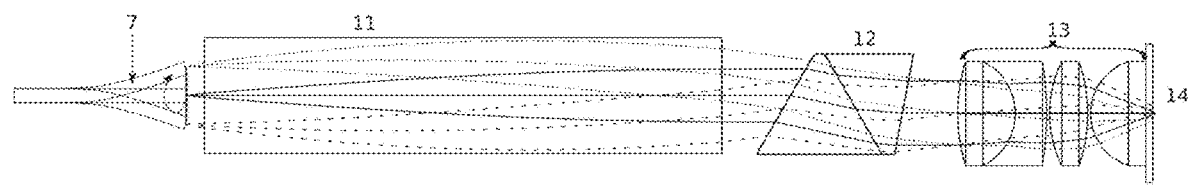

FIG. 5 illustrates another example of the optical arrangement in which the wavelength-dispersive beam combiner 12 is realized by a two-component prism. The prism consists of a crown glass and a flint glass and is designed to produce the required wavelength-selective angular offset while maintaining the direction of the optical axis. The functionality of the other components corresponds to the previous example in FIG. 4.

Figure 6:
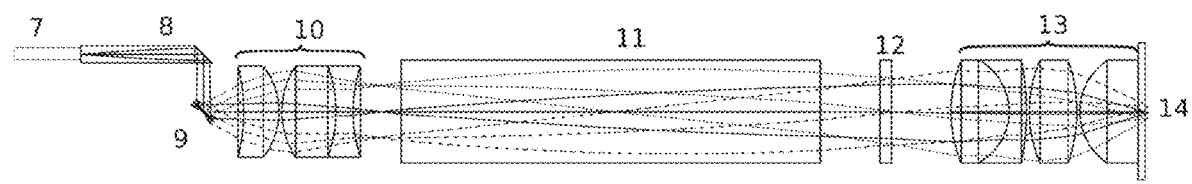
Figure 7:
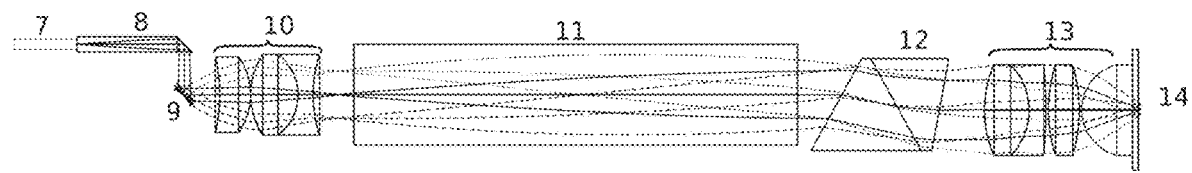

FIG. 6 and FIG. 7 illustrate further examples of the optical arrangement, which are essentially analogous to the examples in FIGS. 4 and 5, but using a MEMS mirror scanner 9, which replaces the fiber scanner. In the examples in FIGS. 6 and 7, the multi-core fiber 7 is attached to a GRIN lens that acts as a collimation unit 8. By means of a prism, a 90° deflected, collimated beam of illumination light is generated. This beam of illumination light is scanned by a MEMS mirror scanner 9 and focused into an intermediate image by a lens group 10 that corrects chromatically and over the image field. This is where an analogous setup begins, as described in the examples of FIGS. 5 and 6.

Figure 8:
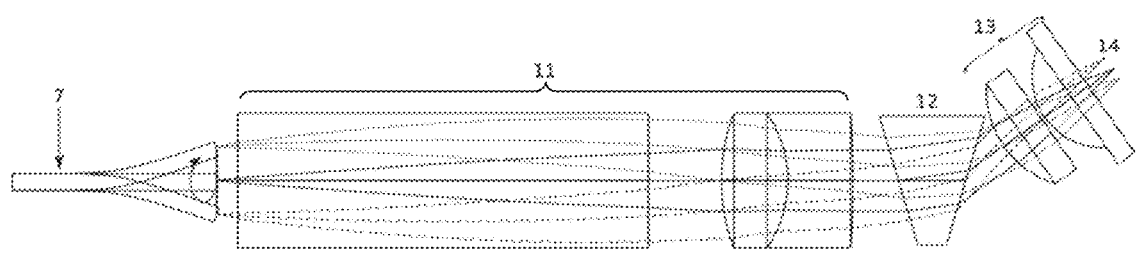

Another example of the optical arrangement is shown in FIG. 8. This shows the possibility of an angled measurement using a prism as wavelength dispersive beam combiner 12. In this example, the beam is deflected by 35 degrees by means of the prism. In this example, the collimation unit 11 is a lens group consisting of a GRIN lens and a doublet lens, and the front lens group 13 is formed by two singlet lenses.

Figure 9:
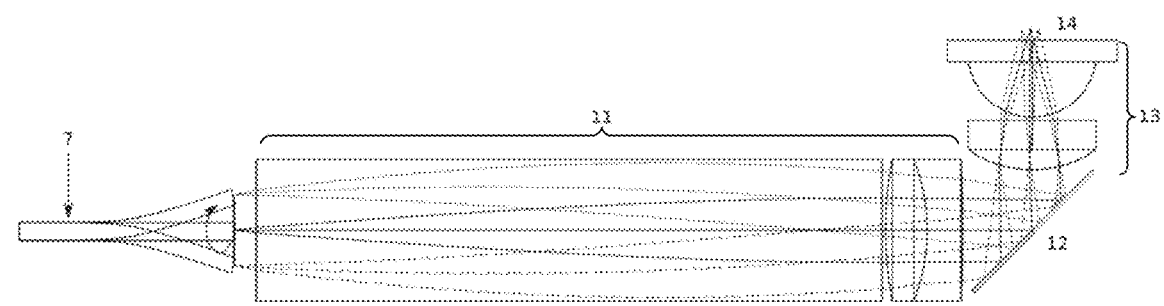

Another example of the optical arrangement is shown in FIG. 9, where a rectangular beam deflection towards the object space 14 is performed, which can be advantageous in endoscopic applications. As in the previous example, the collimation unit 11 can be a lens group consisting of a GRIN lens and a doublet lens, and the front lens group 13 is formed by two singlet lenses. In this example, the wavelength dispersive beam combiner 12 is a linear reflective diffraction grating arranged at 45 degrees to the optical axis and comprising for example a grating period of 55.5 μm per line.

Figure 10:
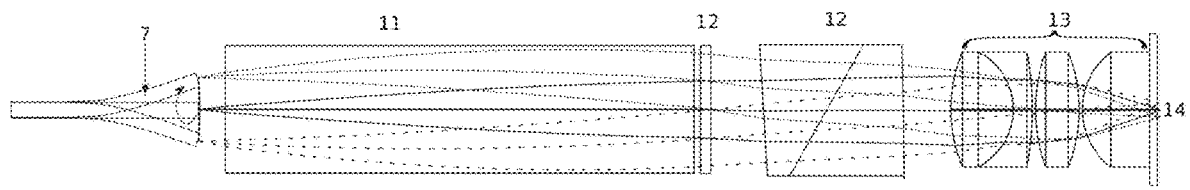

FIG. 10 illustrates an example of the optical arrangement in which the beam combiner 12 is a grating prism (GRISM) consisting of a combination of a diffraction grating and a prism. This offers the possibility to influence the spectral course of the beam deflection in such a way that the shorter-wavelength object light to be detected is not deflected too much laterally from the sample and can be collected efficiently by the light-guiding cladding of the multicore fiber 7, especially if the light-guiding cladding 4 is arranged symmetrically to the fiber cores (as in FIG. 1A).

It is often advantageous that the optical axis of the optical arrangement is not tilted. This is possible in particular by using a transmission grating as wavelength dispersive beam combiner 12, as in the examples of FIGS. 4 and 6, or a double prism 12, as in the examples of FIGS. 5 and 7, or by combining a grating and a prism as in the example of FIG. 10. Under certain circumstances, however, it may also be advantageous to tilt the optical axis within the optical arrangement, for example in the case of an endoscopic probe that is to detect laterally oriented sample areas, e.g. during an endoscopy. In this case it is advantageous to realize the wavelength dispersive beam combiner element 12 as a reflection diffraction grating, as in the example of FIG. 9, or to realize it by a deflection prism, as in the example of FIG. 8.

The invention is not limited by the description based on the exemplary embodiments. Rather, the invention comprises each new feature as well as each combination of features, which in particular includes each combination of features in the claims, even if this feature or combination itself is not explicitly stated in the claims or exemplary embodiments.

The invention claimed is:

1. An optical arrangement comprising:
  a multicore fiber comprising:
    at least a first fiber core configured to guide a first illumination light; and
    a second fiber core configured to guide a second illumination light,
    wherein the multicore fiber comprises a fiber scanner configured to deflect the multicore fiber or the multicore fiber is followed by a mirror scanner;
  a wavelength dispersive beam combiner configured to spatially superimpose the first illumination light and the second illumination light in an object space; and
  a front lens group arranged between the wavelength dispersive beam combiner and the object space,
  wherein the optical arrangement is configured for imaging spectroscopy, and
  wherein the imaging spectroscopy is a Coherent Anti-Stokes Raman Scattering (CARS) spectroscopy or a Stimulated Raman Scattering (SRS) spectroscopy.

2. The optical arrangement according to claim 1, wherein the wavelength dispersive beam combiner is arranged between the fiber scanner or the mirror scanner and the object space.

3. The optical arrangement according to claim 1, further comprising a collimating lens arranged between the fiber scanner or the mirror scanner and the wavelength dispersive beam combiner.

4. The optical arrangement according to claim 1, wherein the multicore fiber comprises a light-guiding cladding configured to guide object light coming from the object space, and wherein the light-guiding cladding is surrounded by an outer cladding comprising a lower refractive index than the light-guiding cladding.

5. The optical arrangement according to claim 4, wherein the multicore fiber comprises an inner cladding in which the fiber cores are disposed, the inner cladding being surrounded by the light-guiding cladding and comprising a lower refractive index than the fiber cores and a lower refractive index than the light-guiding cladding.

6. The optical arrangement according to claim 1, wherein the multicore fiber is a polarization-maintaining fiber for the first and second illumination light guided in the fiber cores.

7. The optical arrangement according to claim 1, wherein the fiber cores are asymmetrically arranged in the multicore fiber.

8. The optical arrangement according to claim 1, wherein the wavelength dispersive beam combiner comprises a transmission diffraction grating, a reflection diffraction grating, a prism or a grating prism.

9. The optical arrangement according to claim 1, wherein the optical arrangement comprises a diameter of less than 5 mm.

10. The optical arrangement according to claim 1, wherein the front lens group is configured to focus the light with a numerical aperture of at least 0.15 into the object space.

11. An endoscopic probe comprising:
  the optical arrangement according to claim 1.

12. A spectroscopic imaging method comprising:
  guiding a first illumination light in a first fiber core of a multicore fiber and guiding a second illumination light in a second fiber core of the multicore fiber, wherein the first illumination light and the second illumination light comprise different wavelengths;
  spatially superimposing the first illumination light and the second illumination light superimposed by a wavelength-dispersive beam combiner in an object space, a front lens group being arranged between the wavelength dispersive beam combiner and the object space,
  wherein the multicore fiber is a fiber scanner or the multicore fiber is followed by a mirror scanner, and wherein the object space is scanned by a movement of the fiber scanner or the mirror scanner; and
  guiding an object light coming from the object space in a light conducting cladding of the multicore fiber in a direction of an evaluation unit,
  wherein the spectroscopic imaging method is a Coherent Anti-Stokes Raman Scattering (CARS) spectroscopy method or a Stimulated Raman Scattering (SRS) spectroscopy method.

13. The method according to claim 12, wherein the wavelength-dispersive beam combiner is arranged between the fiber scanner or the mirror scanner and the object space.

14. The method according to claim 12, wherein a single optical beam path is formed between the multicore fiber and the object space, in which the first and second illumination light are guided in the direction of the object space, and in which the object light is guided in a reverse direction to the multicore fiber.

15. The method according to claim 12, wherein the first illumination light comprises a pump wavelength and the second illumination light comprises a Stokes wavelength.

\* \* \* \* \*